United States Patent [19]

Barrow

[11] Patent Number: 5,010,968
[45] Date of Patent: Apr. 30, 1991

[54] BLOOD AGITATING AND WEIGHING APPARATUS

[76] Inventor: Thomas E. Barrow, Rte. 3, Box 117B, Jacksonville, Tex. 75766

[21] Appl. No.: 441,311

[22] Filed: Nov. 27, 1989

[51] Int. Cl.⁵ ............................................. G01G 13/02
[52] U.S. Cl. .................... 177/118; 177/245; 604/250
[58] Field of Search ............... 604/246, 247, 250, 256, 604/4, 257, 259, 262, 317, 318, 319, 320, 322, 323, 403, 404, 416; 177/118, 245

[56] References Cited

U.S. PATENT DOCUMENTS

| | | | |
|---|---|---|---|
| 2,784,932 | 3/1957 | Poitras | 177/245 X |
| 3,105,490 | 10/1963 | Schoenfeld | 177/245 X |
| 3,616,789 | 11/1971 | Grabhorn | 604/403 X |
| 3,698,494 | 10/1972 | Gaudin | 177/118 |
| 3,960,224 | 6/1976 | Silvers | 177/47 |
| 4,027,735 | 6/1977 | Floyd | 177/118 |
| 4,095,658 | 6/1978 | Kendall et al. | 177/118 |
| 4,378,854 | 4/1983 | Rosen | 177/118 |
| 4,425,114 | 1/1984 | Schoendorfer et al. | 604/7 |
| 4,548,023 | 10/1985 | Danby et al. | 53/452 |
| 4,678,049 | 7/1987 | Gummere et al. | 177/229 |

Primary Examiner—John D. Yasko
Assistant Examiner—Adam J. Cermak
Attorney, Agent, or Firm—Dennis T. Griggs

[57] ABSTRACT

A blood agitating and weighing device includes a base member and a support member, pivotally mounted with respect to the base member, for journally supporting a container, such as a flexible blood storage bag. A spring member is provided for biasing the support member to a first tilted position relative to the base member and a flexible bladder is positioned beneath the support member. The bladder is expandable in response to the introduction of pneumatic pressure therein to overcome the bias of the spring member to move the support member to a second tilted position relative to the base member. The bladder is contracted in response to the release of pneumatic pressure to allow the spring member to move the support member back to the first position. The support member is therefore alternately moved between the first and second positions by the alternating expansion and contraction of the bladder to agitate the blood in the container.

16 Claims, 2 Drawing Sheets

BLOOD AGITATING AND WEIGHING APPARATUS

FIELD OF THE INVENTION

This invention relates generally to apparatus for collecting blood and in particular to an apparatus for agitating collected blood to prevent coagulation thereof and for weighing the collected blood.

1. Background of the Invention

Supplies of blood are maintained by hospitals and other medical facilities for use in blood transfusions. Blood is collected from individual donors at hospitals, clinics and at other sites via mobile blood collection units. Because blood supplies are in great demand, it is important to be able to maintain the quality of blood supplies between the time they are collected and the time they are actually used in transfusions. Typically, the collected blood is mixed with an anticoagulant to prevent the blood from coagulating.

2. Description of the Prior Art

According to prior practice, blood taken from a donor is introduced via a flexible flow tube into a flexible bag or pouch. The pouch is often placed on an agitator device, which rocks the pouch back and forth to mix the blood and anticoagulant. Conventional agitating devices are motorized, and require a source of electrical current as well as relatively expensive electrical components. The agitator may have a scale associated therewith for weighing the collected blood and for cutting off the blood flow to the pouch when a preset weight has been collected.

One problem associated with electrically powered agitators is that a suitable source of electrical power may not be available, such as when blood is collected via mobile collection units. Electrically operated agitators are also relatively large and expensive because of the electrical components required. The need therefore exists in the art for a blood agitator device which can be operated without electrical power.

OBJECTS OF THE INVENTION

It is therefore the principal object of the present invention to provide an improved blood agitator device.

Another object of the invention is to provide a blood agitator device which is operable without electrical power.

Yet another object of the invention is to provide a blood agitator device suitable for use in a mobile blood collection unit.

Still another object of the invention is to provide a device for measuring the weight of blood collected from a donor and for terminating the blood collection process when a predetermined weight of blood has been collected.

A further object of the invention is to provide a pneumatically operated blood agitator device.

SUMMARY OF THE INVENTION

These and other objects are accomplished in accordance with the present invention wherein an agitator device is provided for agitating a liquid, such as blood, collected in a container, such as a flexible blood storage bag. The device includes a base member and a support member for the container, which is pivotally mounted with respect to the base member. In one aspect of the invention the agitating device includes means for biasing the support member to a first tilted position relative to the base member and an expandable member positioned beneath the support member. The expandable member is inflated and expanded in response to the introduction of pneumatic pressure therein to overcome the biasing means to move the support member to a second tilted position, opposite from the first tilted position, relative to the base member. The expandable member is contracted in response to the release of the pneumatic pressure to allow the biasing means to move the support member to the first position. The support member is alternately moved between the first and second tilted positions by the alternating expansion and contraction of the expandable member to agitate the blood in the container.

In one embodiment the device further includes means for introducing pneumatic pressure into the expandable member to inflate the expandable member and for allowing the pneumatic pressure to be released therefrom. In another embodiment the means for introducing pneumatic pressure into the expandable member includes a bellows and a flexible tube coupled between the bellows and the expandable member. The bellows is compressible for transmitting pneumatic pressure through the tube to the expandable member and is inflatable for relieving pneumatic pressure from the expandable member. The bellows is preferably a flexible squeeze bulb operated by hand squeezing action, such as by a blood donor when blood is being collected in the container. When the donor squeezes the bellows, pneumatic pressure is introduced into the expandable member to overcome the biasing means, thereby tilting the support member to the second tilted position. When the donor releases his grip on the bellows, the pneumatic pressure in the expandable member is released back through the flexible tube into the bellows, thereby allowing the expandable member to contract and allowing the biasing means to return the support member to the first tilted position. By alternately squeezing and releasing the bellows, the support member, with the container of blood positioned thereon, is tilted back and forth to agitate the blood for mixing with the anticoagulant in the container.

In another aspect of the invention the agitating device is adapted for controlling the amount of blood being collected in the container via a flexible flow tube extending between the donor and the container. The device includes means for applying tension to the tube so that at least a portion of the tube is maintained relatively straight; means for exerting a compressive force on the relatively straight portion of the tube to close off the tube and terminate the flow of blood to the container; means for monitoring the weight of blood being collected from the donor; latch means for holding the compressive force exerting means out of contact with the relatively straight portion of the tube until a predetermined weight of blood has been collected in the container; and means for releasing the latch means when the predetermined weight of blood has been collected to allow the compressive force exerting means to engage the relatively straight portion of the tube to close off the tube and terminate the blood flow.

In one embodiment the tension applying means includes a retaining member having a pair of aligned slots for receiving the tube therethrough, such that the relatively straight portion of the tube is disposed between the slots. In another embodiment, the compressive force exerting means includes a piston member which is biased toward a first position for closing off the tube when the piston member is in the first position. The piston member further includes a notch therein. The latch means include a bar member having a first end portion which mates with the notch to maintain the piston member in a second position, opposite from the first position, such that the piston member is held out of contact with the tube. The first end portion is disengaged from the notch to release the piston member when sufficient force is exerted on a second end portion of the bar, opposite from the first end portion, to tilt the first end portion away from the piston member.

In the preferred embodiment, the means for monitoring the weight of collected blood includes a tension spring, a first end of which is fixed and a second end of which, opposite from the first end, is movable away from the first end when the spring is under tension. Means is provided for adjusting the tension of the spring in accordance with a predetermined weight of blood to be collected. A platform member is coupled to the second end of the spring and is movable therewith for exerting a downward force on the second end portion of the bar sufficient to tilt the first end portion thereof out of engagement with the piston member when the weight of blood which has been collected causes the second end of the spring and the platform member to move downwardly, such that the platform member contacts the second end portion of the bar.

BRIEF DESCRIPTION OF THE DRAWINGS

Further objects and advantages of the invention will be apparent from the detailed description and claims when read in conjunction with the accompanying drawings wherein:

DETAILED DESCRIPTION OF THE PREFERRED EMBODIMENT

In the description which follows, like parts are marked throughout the specification and drawings, respectively. The drawings are not necessarily to scale and in some instances proportions have been exaggerated in order to more clearly depict certain features of the invention.

Figure 1:
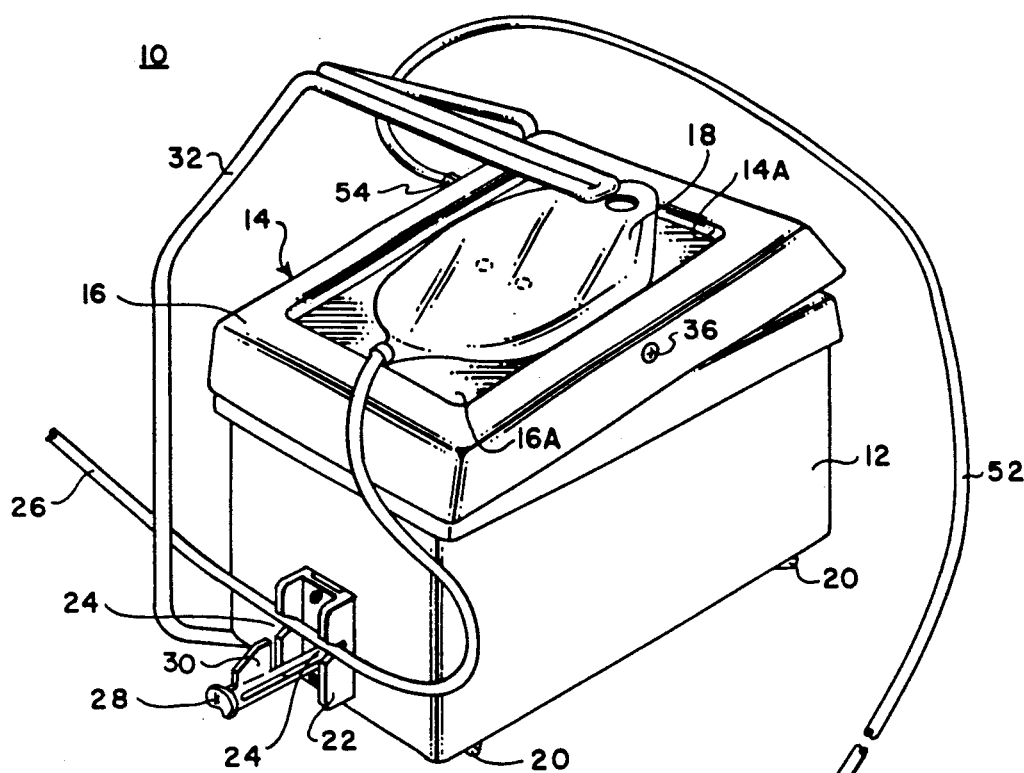
FIG. 1 is a perspective view of a blood agitator and weighing device according to the present invention.

Referring to FIG. 1, a liquid agitator device 10 according to the present invention includes a base member 12 and a support member 14, which is pivotally mounted with respect to base member 12. Support member 14 has a top panel 16 for supporting a liquid container, such as a flexible blood storage bag 18. The support member 14 has a rectangular recess 14A centered about a support panel 16A for receiving the flexible storage bag 18. Base member 12 includes a plurality of bottom feet 20 for stabilizing device 10 on a support surface.

Base member 12 further includes a retaining member 22, projecting outwardly from an end surface of base member 12. Retaining member 22 includes two relatively flat, parallel projections having respective aligned slots 24 for receiving respective portions of a flexible tube 26 as tube 26 passes through retaining member 22. Slots 24 are tapered downwardly and inwardly for tightly gripping tube 26 to exert tension thereon and maintain a portion of tube 26 disposed between aligned slots 24 in a relatively straight orientation. As shown in FIG. 1, one end of tube 26 is coupled to bag 18 and the opposite end of tube 26 is coupled to a blood donor (not shown).

A piston member 28, having an extension portion 30, is provided for closing off tube 26 to terminate the flow of blood from the donor to bag 18 when a predetermined weight of blood has been collected. Piston member 28 is shown in its extended position in FIG. 1 for allowing blood to flow through tube 26. When piston member 28 is retracted, such that extension portion 30 engages the portion of tube 26 disposed between slots 24, tube 26 will be "pinched off" by the inwardly directed force exerted by piston member 28. The operation of piston member 28 will be described in greater detail hereinafter, with respect to FIG. 4. Device 10 also includes a handle 32 to facilitate transport of device 10.

Figure 2:
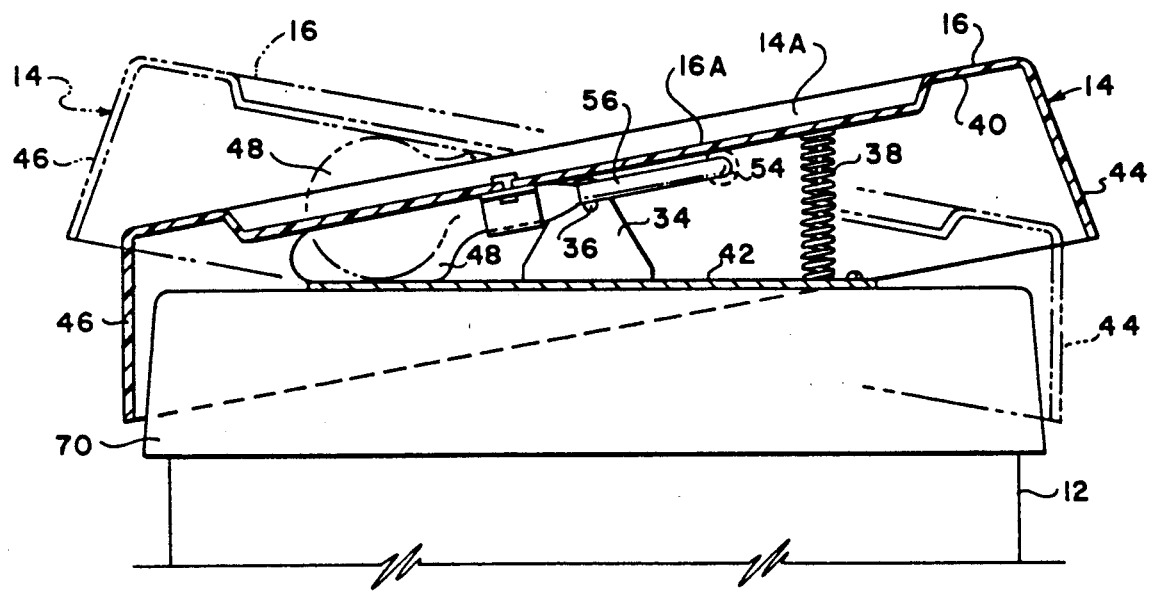
FIG. 2 is a side elevation view of a top portion of the agitator device, illustrating the top portion thereof in different tilted positions for agitating blood collected in a container positioned on top of the agitator device.

Referring to FIGS. 1 and 2, base member 12 includes an upwardly extending member 34 on each side thereof for pivotally mounting support member 14. Each member 34 has a threaded opening therein for receiving a screw 36 or other attachment member to pivotally mount support member 14 with respect to base member 12. Support member 14 can thus be tilted about a horizontal axis substantially coincident with the respective major axes of mounting screws 36.

A compression spring 38 is coupled between an inner surface 40 of support member 14 and a mounting plate 42 fixed to base member 12. Spring 38 is positioned between the horizontal tilt axis and a first end 44 of support member 14 when spring 38 is extended (i.e., not under compression), spring member 38 will bias support member 14 toward a first tilted position at which first end 44 of support member 14 is higher than second end 46 of support member 14, as shown in FIG. 2.

A flexible, inflatable bladder 48 is disposed between inner surface 40 and mounting plate 42 and also between the horizontal tilt axis and second end 46. When support member 14 is in the first tilted position, such that first end 44 is elevated above second end 46, the bladder 48 is in a substantially collapsed position. When pneumatic pressure is introduced into the bladder 48 sufficient to overcome the bias of spring 38, the bladder 48 will be expanded to tilt support member 14 to a second tilted position, opposite from the first tilted position. In a second tilted position, second end 46 is elevated above first end 44, as also shown in FIG. 2.

Pneumatic pressure is introduced into the bladder 48 by means of a squeeze bulb 50 and a pneumatic tube 52. Tube 52 is coupled at one end to bulb 50 and at the opposite end to a nipple 54 projecting outwardly from support member 14. As shown in FIG. 2, another tubular member 56 connects nipple 54 and bladder 48, thereby pneumatically interconnecting bulb 50 and bladder 48.

During the blood collection process, the blood donor is typically placed in a reclining position and a needle is inserted into a vein in the donor's arm to draw blood therefrom. The needle is connected to a flexible flow tube, which in turn is connected to a bag where the blood is collected. To expedite the blood collection process, the donor typically opens and closes the hand on the particular arm in which the needle has been inserted in order to increase the blood flow through the flow tube into the bag.

In accordance with the present invention, the blood donor will alternately squeeze and release bulb 50. The squeezing action will compress bulb 50 to transmit pneumatic pressure to the bladder 48, thereby causing the bladder 48 to expand and tilt support member 14 to the second tilted position. When support member 14 is in the second tilted position, the spring bias of spring 38 is overcome and spring 38 is substantially compressed. When the donor releases his grip on bulb 50, pneumatic pressure will flow from the bladder 48, through tube 52, back into bulb 50, thereby expanding bulb 50 for the next squeeze cycle. The release of pneumatic pressure from the bladder 48 permits it to collapse and allows spring 38 to return to its extended position, thereby tilting support member 14 back to the first tilted position. One skilled in the art will appreciate that as the donor alternately squeezes and releases bulb 50, support member 14 will be tilted gently back and forth to agitate the blood collected in bag 18 and mix the collected blood with the anti-coagulant inside bag 18.

Figure 3:
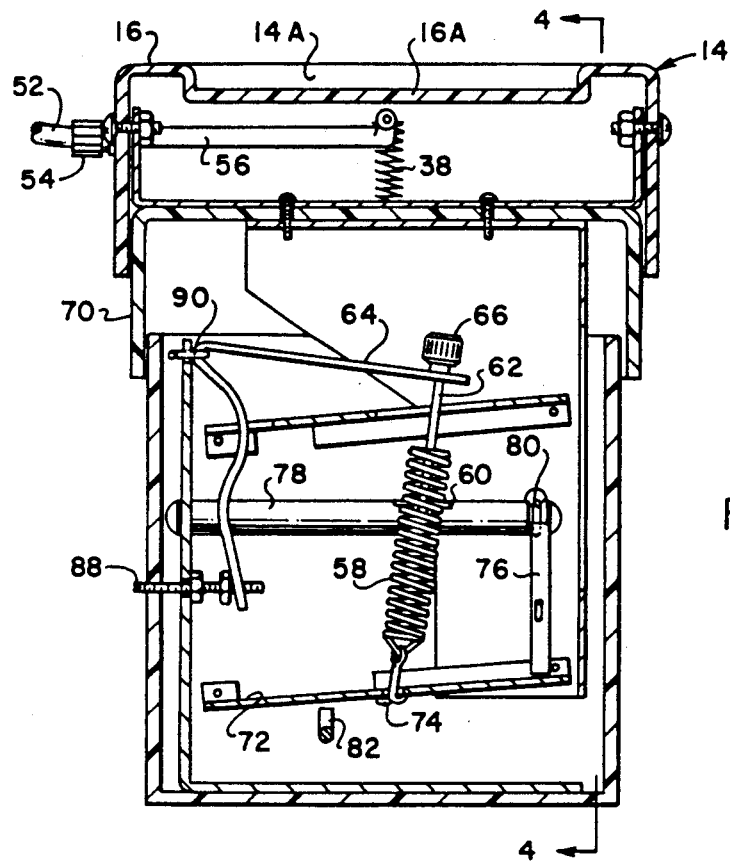
FIG. 3 is a sectional view, taken along the line 3—3 in FIG. 4, showing internal components of the agitator device.
Figure 4:
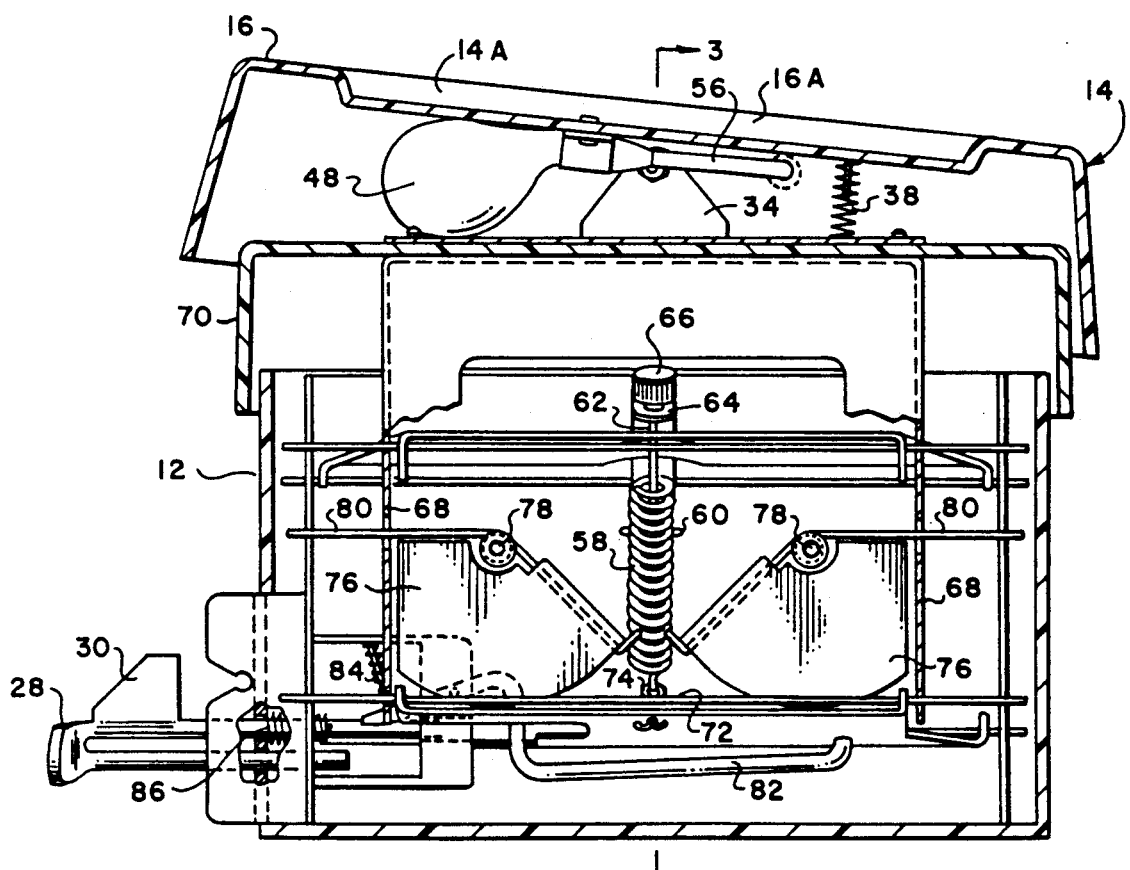
FIG. 4 is a sectional view, taken along the line 4—4 in FIG. 3, showing internal components of the agitator device.

Referring to FIGS. 3 and 4, the agitator device 10 includes means for monitoring the weight of blood or other liquid being collected. The monitoring means includes a tension spring 58 having a relatively flat plate 60 interposed between adjacent turns of spring 58, near the top part of spring 58. A threaded bolt 62 extends through an opening in an elongated arm member 64 and through the top part of spring 58 and terminates substantially at plate 60. Plate 60 maintains the top portion of spring 58, which is disposed between plate 60 and arm member 64, in a fixed position, while allowing the portion of spring 58 below plate 60 to be stretched and compressed depending upon the weight of the liquid in the bag on top of support member 14. An adjustment nut 66 is threadedly connected to bolt 62 for adjusting the tension of spring 58 in order to calibrate device 10, as will be described in greater detail hereinafter.

Spring 58 is disposed within a housing 68, which is movable up and down along with spring 58. Support member 14 and an upper portion 70 of base member 12 are also movable along with housing 68.

Spring 58 is coupled to a bottom portion 72 of housing 68 by means of a cotter pin 74 or other suitable attachment member. A pair of counterweights 76 are mounted on respective shafts 78 for dampening the movement of housing 68 and also to offset variations in the tension of spring 58, which may be caused by changes in humidity, air pressure and other environmental conditions. Counterweights 76 are pivotally mounted on their respective shafts 78 by means of spring rods 80, which extend through respective openings in housing 68. As the weight of the liquid collected in the container on top of support member 14 increases, spring 58 will stretch and housing 68 will move in a downward direction, thereby causing counterweights 76 to rotate upwardly to counteract the downward movement of spring 58 and housing 68.

In accordance with the present invention the flow of liquid to the container disposed on top of support member 14 is cut off after a predetermined weight of liquid has been collected. A substantially Z-shaped bar 82 has a first end portion which mates with a notch disposed in piston member 28, as best seen in FIG. 4. A spring member 84 biases the first end portion of bar 82 into contact with the notch to hold piston member 28 in an extended position, as shown in FIG. 4. A compression spring 86 is disposed on piston member 28 for biasing piston member 28 toward a retracted position. Bar 82 exerts a force acting along the major axis of piston member 28, which is sufficient to overcome the spring bias of spring 86 and hold piston member 28 in the extended position.

A second end portion of Z-shaped bar 82, opposite from the first end portion thereof, is pivotally mounted within base member 12, beneath bottom portion 72 of housing 68. As the weight of the liquid being collected increases, housing 68 will move downwardly along with spring 58 until bottom portion 72 of housing 68 contacts the second end portion of bar 82. The force exerted by bottom portion 72 on the second end portion of bar 82 will pivot bar 82, such that the first end portion thereof will move upwardly and out of mating engagement with the notch in piston member 28. When bar 82 is disengaged from piston member 28, the spring bias of spring 86 will retract piston member 28, such that extension portion 30 of piston member 28 will contact tube 26 (see FIG. 1) and close off the flow of blood to the container on top of support member 14.

Device 10 is calibrated for a predetermined weight of blood to be collected by adjusting the tension of spring 58. As previously mentioned, an adjusting nut 66 is threadedly connected to bolt 62 above arm member 64. Tightening nut 66 by rotating it in a clockwise direction will cause bolt 62 to move upwardly to increase the tension on spring 58, thereby increasing the weight of liquid which must be collected before piston member 28 is released. Similarly, loosening nut 66 by rotating it in a counterclockwise direction will cause bolt 62 to move downwardly to decrease the tension on spring 58, thereby decreasing the weight of liquid which must be collected before piston member 28 is released.

After the initial adjustment of spring tension on spring 58 is accomplished by means of adjustment nut 66, fine adjustment is achieved by means of an adjusting screw 88. Adjusting screw 88 is threadedly received within an opening in arm member 64 at the opposite end thereof from the end at which bolt 62 extends through arm member 64. Arm member 64 is pivotally mounted at a central portion thereof to a fixed portion of base member 12, as indicated at 90 and as best seen in FIG. 3. Turning adjusting screw 88 to the left (counterclockwise) will rotate arm member 64 upwardly (i.e., counterclockwise when viewed from the perspective of FIG. 3), thereby increasing the tension on spring 58. Similarly, turning screw 88 to the right (clockwise) will rotate arm member 64 downwardly (i.e., clockwise when viewed from the perspective of FIG. 3), thereby decreasing the tension on spring 58.

Calibration is achieved by placing a known weight equal to the desired weight of blood to be collected on top of support member 14 and adjusting the tension on spring 58, first by turning nut 66 clockwise to tighten nut 66 and increase the tension on spring 58 until bottom portion 72 of housing 68 contacts the second end portion of bar 82, but does not yet exert sufficient downward force to disengage the first end portion of bar 82 from piston member 28. Further adjustment is made by turning screw 88 counterclockwise to further increase the tension on spring 58 until bar 82 is disengaged from piston member 28, at which point screw 88 is "backed off" approximately ¼ turn clockwise. The above-described procedure has been found to provide a relatively precise calibration of device 10 for the predetermined weight of blood to be collected.

Various embodiments of the invention have been described in detail. Since it is obvious that many changes in and additions to the above-described preferred embodiment can be made without departing from the nature, spirit and scope of the invention, the invention is not limited to said details, except as set forth in the appended claims.

What is claimed is:

1. Apparatus for agitating a liquid collected in container, comprising:

a base member;

a support member for receiving a container, said support member being pivotally mounted onto said base member;

means for biasing said support member to a first tilted position relative to the base member;

an inflatable member disposed between said support member and said base member; and, means for introducing pneumatic pressure into said inflatable member to expand said inflatable member and for allowing said pneumatic pressure to be released therefrom.

2. The apparatus of claim 1 wherein said means for introducing pneumatic pressure includes a bellows and a flexible tube coupled between said bellows and said inflatable member, said bellows being compressible for transmitting pneumatic pressure through said tube to said inflatable member and being expandable for relieving pneumatic pressure from said inflatable member.

3. The apparatus of claim 2 wherein said bellows is manually operable, said bellows being compressed by hand squeezing action to introduce pneumatic pressure into said inflatable member and being expanded by the release of pneumatic pressure from said inflatable member into said bellows.

4. The apparatus of claim 2 wherein said bellows comprises a flexible bulbous member which is adapted to be gripped by a donor's hand.

5. The apparatus of claim 1 wherein said inflatable member is an inflatable bladder.

6. The apparatus of claim 1 wherein said biasing means includes a compression spring member.

7. Apparatus for controlling the amount of blood being collected in a container via a flexible tube extending between the container and a blood donor, comprising in combination:

a base member;

means coupled to said base member for applying tension to said tube so that at least a portion of said tube is maintained relatively straight;

means coupled to said base member for exerting a compressive force on said relatively straight portion of said tube to close off said tube and terminate the flow of blood to the means coupled to said base member for detecting a predetermined weight of blood collected in the container;

latch means for holding said compressive force exerting means out of contact with said relatively straight portion of said tube until a predetermined weight of blood has been collected in said container;

means for releasing said latch means when a predetermined weight of blood has been collected to allow said compressive force exerting means to engage said relatively straight portion of said tube to close off the tube and terminate the blood flow;

said tension applying means including a retaining member having a pair of aligned slots for receiving the flexible tube therethrough; and, said compressive force exerting means including a piston member which is biased toward a first position for closing off the flexible tube, said piston member having a notch therein, said latch means including a bar member pivotally mounted on said base member, said bar member having a first end portion which mates with said notch to maintain said piston member in a second position opposite from said first position, such that said piston member is held out of contact with the flexible tube, the first end portion of said bar member being disengaged from said notch to release said piston member when a force is exerted on a second end portion of said bar member, opposite from the first end portion thereof, to tilt said first end portion away from said piston member.

8. The apparatus of claim 7 further including a spring member for biasing the first end portion of said bar member toward said piston member to maintain said first end portion in mating engagement with said notch.

9. The apparatus of claim 8 including counterweight means coupled to said spring member for opposing extension thereof.

10. The apparatus of claim 7, further including means for exerting a downward force on said second end portion of said bar member sufficient to tilt said first end portion out of engagement with said piston member when said predetermined weight of blood has been collected.

11. Apparatus for agitating blood in a blood storage container of the type having a flexible tube adapted for conveying blood from a donor to the storage container comprising, in combination:

a base member;

a support member for supporting a blood storage container, said support member being pivotally mounted with respect to the base member;

means for biasing the support member to a first tilted position relative to the base member;

an expandable member positioned between the support member and the base member, said expandable member being responsive to the introduction of pneumatic pressure therein to overcome said biasing means and move said support member to a second tilted position relative to the base member, opposite from a first tilted position, and said expandable member being deflatable and contractible in response to the release of said pneumatic pressure therefrom to allow said biasing means to move said support member to said first position, said support member being alternately movable between said first and second positions by the alternating expansion and contraction of said expandable member to agitate blood collected in the container;

means for exerting a compressive force on the flexible tube to close off the tube and terminate the flow of blood to the container; and means for controlling said compressive force exerting means to hold said compressive force exerting means out of contact with the flexible tube until a predetermined weight of blood has been collected in said container and for releasing said compressive force exerting means to contact the flexible tube when a predetermined weight of blood has been collected.

12. Blood collection apparatus as defined in claim 11 further including means for introducing pneumatic pressure into said expandable member and for releasing said pneumatic pressure therefrom to collapse and contract said expandable member.

13. Blood collection apparatus as defined in claim 12 wherein said means for introducing pneumatic pressure includes a bellows and a flexible tube coupled between said bellows and said expandable member, said bellows being compressible for transmitting pneumatic pressure through said tube to said expandable member and being inflatable for releasing pneumatic pressure from said expandable member.

14. Blood collection apparatus as defined in claim 11 wherein said means for controlling said compressive force exerting means includes:
   means for monitoring the weight of blood being collected in the container;
   latch means for holding said compressive force exerting means out of contact with said relatively straight portion of said tube until the predetermined amount of blood has been collected in the container; and
   means for releasing said latch means when the predetermined weight of blood has been collected to allow said compressive force exerting means to contact said relatively straight portion of said tube to close off said tube and terminate the blood flow.

15. Blood collection apparatus as defined in claim 11 wherein said tension applying means includes a retaining member having a pair of aligned slots for receiving said tube therethrough.

16. Blood collection apparatus as defined in claim 11 wherein said compressive force exerting means includes a piston member which is biased toward a first position for closing off said tube, said piston member having a notch therein, said means for controlling said compressive force exerting means including a bar member pivotally mounted in said base member, said bar member having a first end portion which mates with said notch to maintain said piston member in a second position, opposite from said first position, such that said piston member is prevented from contacting said tube, said first end portion being disengagable from said notch to release said piston member when a force is exerted on a second end portion of said bar member, opposite from the first end portion thereof, to tilt said first end portion out of engagement from said piston member.

* * * * *

UNITED STATES PATENT AND TRADEMARK OFFICE
CERTIFICATE OF CORRECTION

PATENT NO.   : 5,010,968

DATED        : 04/30/91

INVENTOR(S)  : Thomas E. Barrow

It is certified that error appears in the above-identified patent and that said Letters Patent is hereby corrected as shown below:

Column 7, line 12, "in container" should be -- in a container --.

Column 7, line 57, "blood to the" should be -- blood to the container;--.

Signed and Sealed this

Twenty-fifth Day of August, 1992

Attest:

DOUGLAS B. COMER

*Attesting Officer*     Acting Commissioner of Patents and Trademarks